United States Patent
Watanabe et al.

(10) Patent No.: US 10,314,769 B2
(45) Date of Patent: Jun. 11, 2019

(54) ORGANIC-INORGANIC COMPOSITE PARTICLES AND COSMETIC PRODUCT

(71) Applicant: JGC Catalysts and Chemicals Ltd., Kanagawa (JP)

(72) Inventors: Satoshi Watanabe, Fukuoka (JP); Naoyuki Enomoto, Fukuoka (JP); Ikuko Shimazaki, Fukuoka (JP)

(73) Assignee: JGC Catalysts and Chemicals Ltd., Kanagawa (JP)

( * ) Notice: Subject to any disclaimer, the term of this patent is extended or adjusted under 35 U.S.C. 154(b) by 0 days.

(21) Appl. No.: 15/939,697

(22) Filed: Mar. 29, 2018

(65) Prior Publication Data

US 2018/0280256 A1 Oct. 4, 2018

(30) Foreign Application Priority Data

Mar. 31, 2017 (JP) .................... 2017-072496

(51) Int. Cl.
| | | |
|---|---|---|
| *A61K 8/02* | (2006.01) | |
| *A61Q 19/00* | (2006.01) | |
| *A61K 8/25* | (2006.01) | |
| *A61K 8/73* | (2006.01) | |

(52) U.S. Cl.
CPC ............ *A61K 8/0241* (2013.01); *A61K 8/25* (2013.01); *A61K 8/731* (2013.01); *A61Q 19/00* (2013.01); *A61K 2800/10* (2013.01); *A61K 2800/412* (2013.01); *A61K 2800/413* (2013.01); *A61K 2800/5426* (2013.01); *A61K 2800/592* (2013.01)

(58) Field of Classification Search
CPC .... A61K 8/25; A61K 2800/10; A61K 28/412; A61Q 19/00
See application file for complete search history.

(56) References Cited

U.S. PATENT DOCUMENTS

2011/0287105 A1  11/2011  Gittleman

FOREIGN PATENT DOCUMENTS

| JP | H07-196312 | 8/1995 |
| JP | 2002-265257 A | 9/2002 |
| JP | 2013-527204 A | 6/2013 |
| JP | 2013-136732 A | 7/2013 |
| JP | 2014-043566 A | 3/2014 |

OTHER PUBLICATIONS

Huang et al, Effects of Compositional Tailoring on Drug Delivery Behaviours of Silica Xerogel /Polymer Core-Shell omposite Nanoparticles, Scientific Reports 8, Article No. 13002 (2018).*

* cited by examiner

*Primary Examiner* — Carlos A Azpuru
(74) *Attorney, Agent, or Firm* — Alston & Bird LLP

(57) ABSTRACT

The present invention provides organic-inorganic composite particles having a suitable biodegradability. The organic-inorganic composite particles of the present invention include a silica component and a biodegradable plastic. The organic-inorganic composite particles have a mean particle diameter (d1) ranging from 0.5 μm to 25 μm, an absolute specific gravity greater than 1.0 g/cm3 and equal to or smaller than 2.0 g/cm3, and a contact angle with water of 90° or less. A cosmetic product including the organic-inorganic composite particles has good texture characteristics.

8 Claims, No Drawings

ORGANIC-INORGANIC COMPOSITE PARTICLES AND COSMETIC PRODUCT

CROSS REFERENCE TO RELATED APPLICATIONS

This application claims priority to and the benefit of Japanese Patent Application No. 2017-072496, filed on Mar. 31, 2017, the contents of which as are hereby incorporated by reference in their entirety herein.

BACKGROUND

Related Field

The present invention relates to spherical organic-inorganic composite particles having a suitable biodegradability, and a cosmetic product including the organic-inorganic composite particles.

Description of Related Art

Today, synthetic polymers (plastics) derived from petroleum are being used in various industries, and support the convenience in our lives. Many of the synthetic polymers have been developed to secure long-term stability. Therefore, the synthetic polymers remain in natural environments without being decomposed, and cause various environmental problems. For example, plastic products that have arrived at a water environment are accumulated there for a long time, and cause serious damage to the ecosystems of oceans and inland waters. Further, so-called micro plastics, which are fine plastics of which the length ranges from 5 mm to nano levels, have recently been considered as another serious problem. Examples of the micro plastics include personal consumable products such as cosmetics, small masses of yet-to-be processed plastic resins, micro-pieces resulting from pulverization of large products floating in oceans.

Recent facial cleaners include plastic particles (e.g., polyethylene particles) having a size in orders of several hundreds of micrometers, so that the facial cleaners feel coarse and have an increased cleaning effect. Plastic particles, of which an absolute specific gravity is small, are difficult to eliminate at sewage-treatment plants, and flow into rivers, oceans, inland waters, and other water environments. Further, plastic particles tend to absorb chemical substances such as insecticides. Such plastic particles accumulate and concentrate in the bodies of fish and shellfish. It is possible that human bodies are adversely affected by such fish and shellfish. This problem has been pointed out by United Nations Environment Programme and other organizations. Various countries and industry associations are considering framing regulations against this problem.

In view of the foregoing background, biodegradable plastics, which are decomposed into water and carbon dioxide by, for example, microorganisms in a natural environment to be incorporated in a natural carbon cycle, are developed intensively and worldwide. For example, Japanese Unexamined Patent Publication No. 2013-136732 discloses a cleaning agent including biodegradable plastic fiber-like particles having a particle diameter of 425 μm or more. Japanese Unexamined Patent Publication (Japanese Translation of PCT Application) No. 2013-527204 discloses a polylactic acid having an average particle size ranging from 1 μm to 44 μm and being suitable for use in a cosmetic composition. Japanese Unexamined Patent Publication No. 2014-43566 discloses, as biodegradable microparticles, a polylactic acid-based resin microparticles having a number average particle diameter less than 1 μm.

BRIEF SUMMARY

The biodegradable plastic particles of the known art need a long time to naturally decompose if the plastic particles have a large particle size. The finer particles sizes are, the shorter the time necessary for natural decomposition becomes. However, microparticles firmly adhere to each other, and have a low flowability. If such microparticles are blended, as a texture improver, in a cosmetic product, the particles exhibit a strong adhesiveness. Thus, the microparticles of the known art are not suitable as a texture improver which is required to have an appropriate spreadability. Further, biodegradable polymers of the known art, which float on water and tend to absorb hazardous chemical substances and concentrate, cause environmental problems.

In view of the foregoing problems, it is therefore an object of the present invention to provide organic-inorganic composite particles which have a suitable biodegradability, do not float on water, and have a reduced tendency to absorb hazardous chemical substances. The organic-inorganic composite particles having these characteristics are less likely to cause environmental problems and have a suitable flowability. Thus, the organic-inorganic composite particles can be put, with security, to the same uses as those for plastic beads. The organic-inorganic composite particles having these characteristics can be blended as a texture improver in a cosmetic product.

Organic-inorganic composite particles according to an aspect of the present invention include a silica component and a biodegradable plastic, and have a mean particle diameter ($d_1$) ranging from 0.5 μm to 25 μm, an absolute specific gravity greater than 1.0 g/cm$^3$ and equal to or smaller than 2.0 g/cm$^3$, and a contact angle with water of 90° or less.

According to an aspect of the present invention, the organic-inorganic composite particles have a specific surface area (measured by the BET method) of 5 m$^2$/cm$^3$ or more and less than 60 m$^2$/cm$^3$. The organic-inorganic composite particles have a modulus of elasticity ranging from 2 GPa to 30 GPa.

According to an aspect of the present invention, the organic-inorganic composite particles have a mean particle diameter ($d_3$) after being subjected to ultrasonic dispersion in which a dispersion liquid of the organic-inorganic composite particles is ultrasonically dispersed using an ultrasonic disperser, and a ratio ($d_3/d_1$) between the mean particle diameter ($d_3$) after the ultrasonic dispersion and the mean particle diameter ($d_1$) before the ultrasonic dispersion is within the range of ±0.05. According to an aspect of the present invention, the organic-inorganic composite particles preferably include the silica at a rate from 1 wt. % to 80 wt. %, and the biodegradability plastic at a rate from 20 wt. % to 99 wt. %.

A cosmetic product of the present invention includes the organic-inorganic composite particles of any one of the foregoing aspects.

The organic-inorganic composite particles of the present invention do not float on water and have a reduced tendency to absorb hazardous water-insoluble chemical substances. In addition, the organic-inorganic composite particles have a suitable biodegradability, and thus, are less likely to cause environmental problems.

DETAILED DESCRIPTION OF VARIOUS EMBODIMENTS

Organic-inorganic composite particles of the present invention are spherical particles and include a silica component and a biodegradable plastic. The organic-inorganic composite particles have a mean particle diameter ($d_1$) ranging from 0.5 μm to 25 μm, an absolute specific gravity greater than 1.0 g/cm$^3$ and equal to or smaller than 2.0 g/cm$^3$, and a contact angle with water of 90° or less. The mean particle diameter ($d_1$) can be determined by a laser diffraction method. If the organic-inorganic composite particles had a mean particle diameter smaller than 0.5 μm, the texture characteristics of a cosmetic product containing the organic-inorganic composite particles, such as rolling effect, duration of rolling effect, and uniform spreadability would be deteriorated significantly. If the organic-inorganic composite particles had a mean particle diameter greater than 25 μm, a powder of the particles would feel coarse, less soft and less moist. It is more preferable that the mean particle diameter ($d_1$) range from 2 μm to 10 μm.

If the organic-inorganic composite particles had an absolute specific gravity smaller than 1.0 g/cm$^3$, the organic-inorganic composite particles would float on water in a water environment, which would reduce a biodegradation rate. If the organic-inorganic composite particles had an absolute specific gravity greater than 2.0 g/cm$^3$, a content of the biodegradable plastic would decrease, and consequently, it would become difficult to obtain desired texture characteristics similar to those of plastic particles. It is particularly preferable that the organic-inorganic composite particles have an absolute specific gravity ranging from 1.1 g/cm$^3$ to 1.8 g/cm$^3$.

Organic-inorganic composite particle having a contact angle with water greater than 90° tends to float on water in a water environment, which may reduce a biodegradation rate. The contact angle with water of the organic-inorganic composite particles of the present invention is preferably smaller than 80°, and more preferably 70° or less. The contact angle depends on the properties of the biodegradable plastic that is a constituent component of the organic-inorganic composite particles. If the biodegradable plastic is hydrophobic, the organic-inorganic composite particles generally have a contact angle greater than 90°. In such a case, addition of a surfactant or other agents to the organic-inorganic composite particles can reduce the contact angle to 90° or less. Hydrophilic organic-inorganic composite particles having a contact angle of 90° or less have a reduced tendency to lower a biodegradation rate, and a reduced tendency to absorb water-insoluble hazardous chemical substances such as polychlorinated biphenyl compounds and insecticides.

The organic-inorganic composite particles preferably have a specific surface area per unit volume, determined by the BET method, ranging from 5 m$^2$/cm$^3$ to 60 m$^2$/cm$^3$. The organic-inorganic composite particles having a specific surface area smaller than 5 m$^2$/cm$^3$ may have a reduced biodegradability. The organic-inorganic composite particles having a specific surface area of 60 m$^2$/cm$^3$ or more are categorized as a nanomaterial, and may become difficult to put to the same uses as those for the known plastic beads. It is particularly preferable that the specific surface area be equal to or greater than 10 m$^2$/cm$^3$ and smaller than 60 m$^2$/cm$^3$.

It is preferable that the organic-inorganic composite particles have a modulus of elasticity within the range from 2 GPa to 30 GPa. The modulus of elasticity can be determined by a micro compression test. A modulus of elasticity smaller than 2 GPa may result in a decrease in the strength of compressed product such as a powder foundation. This may lead to limitation of an amount of the organic-inorganic composite particles to be blended. A modulus of elasticity greater than 30 GPa makes the organic-inorganic composite particles less deformable in response to stress, and less soft and moist than plastic beads. It is particularly preferable that the modulus of elasticity be within the range from 3 GPa to 20 GPa.

If the organic-inorganic composite particles are used in a cosmetic product, the particles may collapse during the manufacturing process of the cosmetic product, and the resultant cosmetic product may not have a function as initially expected. To address this problem, it is preferable that the mean particle diameter of the particles exhibit a rate of change remaining substantially the same before and after application of ultrasound to a dispersion liquid of the particles. Specifically, the organic-inorganic composite particles are dispersed in distilled water to obtain a dispersion liquid. The dispersion liquid is to an ultrasonic disperser to be dispersed for 60 minutes. The ratio ($d_3/d_1$) between the mean particle diameter ($d_3$) after the dispersion test and the mean particle diameter ($d_1$) before the dispersion test is preferably within the range of ±0.05. A ratio between the mean particle diameters smaller than −5% means that the particles have a low strength and may collapse due to a mechanical load applied in the manufacturing process of a cosmetic product or other similar products, and that desired texture improvement may not be achieved. A ratio between the mean particle diameters greater than 5% means that the biodegradable plastic swells in water. As a result, the viscosity of the manufactured cosmetic product and other products tends to increase, making it impossible to ensure quality stability. This may also change the texture characteristics. It is particularly preferable that the ratio ($d_3/d_1$) between the mean particle diameters be within the range of ±3%.

The organic-inorganic composite particles include the silica component at a rate ranging from 1 wt. % to 80 wt. %, and the biodegradability plastic at a rate ranging from 20 wt. % to 99% wt. %. If the rate of the silica component were less than 1 wt. %, the effect of the silica component as a binder would decreases. In addition, the number of contact points among the microparticles of the biodegradable plastic would increase, making it difficult to separate the microparticles from each other again. If the rate of the biodegradable plastic is less than 20 wt. %, the biodegradable plastic could not provide desired soft texture and moist texture that are unique to plastic beads. It is particularly preferable that the organic-inorganic composite particles include the silica component at a rate ranging from 5 wt. % to 80 wt. %, and the biodegradability plastic at a rate ranging from 20 wt. % to 95 wt. %.

It is preferable that the organic-inorganic composite particles have a sphericity ranging from 0.85 to 1.00. The sphericity can be determined by image analysis of a scanning electron microscope photograph. If the sphericity were less than 0.85, the duration of rolling effect would significantly decrease when a cosmetic product containing the organic-inorganic composite particles is applied onto skin.

Further, the organic-inorganic composite particles may include, instead of the silica-based particles, inorganic oxide microparticles including at least one of titanium oxide, an iron oxide, or zinc oxide, provided that the rate of the inorganic oxide microparticles is 20 wt. % or less. Within this range, the organic-inorganic composite particles can contain the inorganic oxide microparticles uniformly. Preferable examples of the iron oxide include ferric oxide, α-iron oxyhydroxide, and triiron tetroxide. It is preferable that the inorganic oxide microparticles have a mean particle diameter substantially equivalent to that of the silica-based particles. Thus, the mean particle diameter of the inorganic oxide microparticles is suitably within the range from 100 nm to 1000 nm.

A silica component and a biodegradable plastic included in the organic-inorganic composite particles of the present invention will be described in detail below.

<Silica Component>

Examples of the silica component contained in the organic-inorganic composite particles include a silicate binder and silica-based particles. For example, the silicate binder can be prepared through dealkalization of (e.g., removal of Na ions from) a silicate aqueous solution of an alkali metal silicate or an organic base silicate using a cation-exchange resin. Examples of the silicate include alkali metal silicates such as sodium silicate (water glass) and potassium silicate, and organic base silicates such as quaternary ammonium silicate.

A silica-based particle as used herein means an inorganic oxide particle containing silica, and examples thereof include complex oxides such as a silica-alumina complex oxide, a silica-zirconia complex oxide, and silica-titania complex oxide, and silica. The manufacturing conditions of the organic-inorganic composite particles do not need to be changed depending on difference in the composition of the silica-based particles. Taking into account inclusion of the organic-inorganic composite particles in a cosmetic product, amorphous silica is suitably used as the silica-based particles.

It is preferable that the silica-based particles have a mean particle diameter ($d_2$) ranging from 5 nm to 1 μm. The mean particle diameter is particularly preferably within the range from 10 nm to 0.5 μm. If the mean particle diameter were greater than 1 μm, a binder effect of the biodegradable particles would decrease and the dissolution rate of silica in water environment would decrease, resulting in undesired deterioration of the suitable biodegradability. If the mean particle diameter were less than 5 nm, the stability of the silica microparticles would decrease. Such a decrease in the stability is industrially undesirable.

To realize a sustainable society, it is preferable to use a silica component produced from a plant-derived raw material. In many countries including Europe and America, there is an increasing demand for organic cosmetic products, in view of harmony with environment and importance of safety. ISO 16128-1 (Guidelines on technical definitions and criteria for natural and organic cosmetic ingredients and products Part 1: Definitions for ingredients) defines the raw materials for the organic cosmetic products. Silica sand that is used widely as a source of silica is classified as a mineral component, whereas a plant-derived silica component is classified as a natural component. Thus, such a plant-derived silica meets the demand.

Grasses contain a large amount of plant-derived silica components. Specifically, the plant-derived silica components can be extracted from rice chaff and rise ears. For example, it has been known that high-purity silica can be obtained by the burning method disclosed in Japanese Unexamined Patent Publication No. H7-196312, a compressed hot water method disclosed in Japanese Unexamined Patent Publication No. 2002-265257, and other methods. A plant-derived silica component obtained by such a method is dissolved with sodium hydroxide to obtain sodium silicate. Then, silica particles can be prepared according to a common manner.

<Biodegradable Plastic Particles>

Although a large amount of petroleum-derived biodegradable plastics are used industrially, the biodegradable plastic for the organic-inorganic composite particles of the present invention is not limited to any particular raw materials as long as the biodegradability is achieved. However, to realize a sustainable society, it is preferable to use a biomass plastic that is a renewable organic source, as the biodegradable plastic. Example of the biomass plastic include a chemically-synthesized polylactic acid, polycaprolactone, polybutylene succinate, polyethylene succinate, polyvinyl alcohol, polyaspartic acid, a microbially-produced pullulan, polyglutamic acid, polyhydroxyalkane acid, plant- or animal-derived starch, cellulose, amylose, chitin, and chitosan. The plant-derived cellulose is particularly suitable in terms of quality, price, marketed amount, and safety.

It is preferable to use, as the biodegradable plastic, biodegradable plastic particles having a mean particle diameter ($d_4$) ranging from 1 nm to 1 μm. Organic-inorganic composite particles produced using the biodegradable plastic particles having such a micro mean particle diameter can exhibit a suitable biodegradability. It is particularly preferable that the mean particle diameter of the biodegradable plastic particles be within the range from 0.1 μm to 0.5 μm. Apart from the particles described above, cellulose nanofibers having a thickness ranging from 1 nm to 500 nm and a length of 1 μm or more (measurement based on an electron microscope photograph), and cellulose nanocrystals having a thickness ranging from 10 nm to 50 nm and a length ranging from 100 nm to 500 nm (measurement based on an electron microscope photograph) can also be suitably used as the biodegradable plastic.

<Method for Producing Organic-Inorganic Composite Particles>

A method for producing the organic-inorganic composite particles of the present invention will be described next. The method for producing the organic-inorganic composite particles of the present invention includes Step A of preparing a dispersion liquid by mixing a liquid containing a silica component and a liquid containing a biodegradable plastic together, and a Step B of preparing the organic-inorganic composite particles by granulating a solid content in the dispersion liquid.

The steps will be described in detail below.

<Step A>

A silica sol may be used as the silica component. In this case, a silica sol containing 1-30 wt. % of silica-based particles in terms of solid content is prepared. An aqueous dispersion liquid containing biodegradable plastic particles at a solid content concentration of 1-50 wt. % is added to the silica sol, thereby preparing slurry.

Alternatively, a silicate binder may be used as the silica component. In this case, a silicate binder having a solid content concentration of 1.5-10.0 wt. % is prepared. A silicate binder having a solid content concentration of 2.0-5.0 wt. % is particularly suitable. If the solid content concentration were greater than 10.0 wt. %, the silicate binder would decrease in stability, and silica in a micro gel or particle state would be produced over time. This causes an increase in specific surface area.

<Step B>

Granulating may be performed by a generally known method such as a spray drying process and an emulsification process.

For example, according to the spray drying method using a spray dryer, the organic-inorganic composite particles are obtained by spraying a spray liquid into hot airflow at a rate of 1-3 L/min. At this time, the hot airflow preferably has an inlet temperature within the range from 70° C. to 200° C. and an outlet temperature within the range from 40° C. to 60° C. If the inlet temperature was lower than 70° C., the solid content in the dispersion liquid would be dried insufficiently. If the inlet temperature was higher than 200° C., the biodegradable plastic might decompose. If the outlet temperature was lower than 40° C., the solid content would be inadequately dried and adhere to the inside of the apparatus. The inlet temperature is more preferably within the range from 100° C. to 150° C.

According to the emulsification process, an emulsion is prepared by mixing the slurry described above with a water-insoluble organic solvent containing a surfactant, and the emulsion is heated and dehydrated, thereby obtaining the organic-inorganic composite particles.

Further, a liquid prepared through dealkalization of (e.g., removal of Na ions from) a silicate aqueous solution of an alkali metal silicate or an organic base silicate using a cation-exchange resin may be used as the silicate binder. Examples of the silicate include alkali metal silicates such as sodium silicate (water glass) and potassium silicate, and organic base silicates such as quaternary ammonium silicate.

If necessary, the spray liquid may contain inorganic oxide microparticles as a metal oxide other than silica. It is preferable that the inorganic oxide microparticles have a mean particle diameter substantially equivalent to that of the silica-based particles. Specifically, the mean particle diameter of the inorganic oxide microparticles ranges from 100 nm to 1000 nm. The inorganic oxide microparticles have such optical characteristics that the microparticles applied on skin cover the skin and block UV. The inorganic oxide microparticles can be applied to the skin without having a rough texture, and contribute to achievement of texture characteristics including a highly slidable texture and of the optical characteristics.

Further, organic-inorganic composite particles including organic microparticles may be heated at 400-1200° C. under atmospheric pressure or a reduced pressure to remove the organic microparticles. This enables preparation of organic-inorganic composite particle having a larger pore volume.

<Cosmetic Product>

Cosmetic products produced by blending the organic-inorganic composite particles with various cosmetic ingredients will be described in detail below. Note that the present invention is not limited to the following cosmetic products.

Unlike the known particles consisting of a single inorganic component such as silica particles, the organic-inorganic composite particles of the present invention used in a cosmetic product can provide main texture characteristics required for a texture improver for cosmetic products. Specifically, the particles of the present invention provide not only the rolling effect, the duration of rolling effect, and the uniform spreadability, but also soft texture and moist texture that are unique to plastic beads.

Examples the cosmetic ingredients include: fats and oils such as olive oil, rape oil, and beef tallow; waxes such as jojoba oil, carnauba wax, candelilla wax, and beeswax; paraffin; squalane; synthetic and vegetable squalane; α-olefin oligomer; microcrystalline wax; hydrocarbons such as pentane and hexane; fatty acids such as stearic acid, myristic acid, oleic acid, and α-hydroxy acid; alcohols such as isostearyl alcohol, octyldodecanol, lauryl alcohol, ethanol, isopropanol, butyl alcohol, myristyl alcohol, cetanol, stearyl alcohol, and behenyl alcohol; alkyl glyceryl ethers; esters such as isopropyl myristate, isopropyl palmitate, ethyl stearate, ethyl oleate, cetyl laurate, and decyl oleate; polyhydric alcohols such as ethylene glycol, triethylene glycol, polyethylene glycol, propylene glycol, glycerin, and diglycerin saccharides such as sorbitol, glucose, sucrose, and trehalose; silicone oils such as methyl polysiloxane, methyl hydrogen polysiloxane, methyl phenyl silicone oil, various modified silicone oils, and cyclic dimethyl silicone oil; silicone gels crosslinked by silicone-based or other organic compounds; nonionic, cationic, anionic, and amphoteric surfactants; fluorine oils such as perfluoro polyether; gum arabic, carrageenan, agar-agar, xanthan gum, gelatin, alginic acid, guar gum, albumin, pullulan, carboxyvinyl polymer, cellulose, and derivatives thereof; polymers such as amid polyacrylate, sodium polyacrylate, and polyvinyl alcohol; anionic, cationic, and nonionic surfactants; animal or plant extracts; amino acids and peptides; vitamins; cinnamic acid-based ultraviolet screening agents (e.g., octyl p-methoxy cinnamate-based ultraviolet screening agent), salicylic acid-based, benzoic ester-based, urocanic acid-based, and a benzophenone-based ultraviolet screening agents; an antiseptic and preservative agent; an antioxidant; a modified or unmodified clay mineral; solvents such as butyl acetate, acetone, and toluene; titanium oxide having various particle diameters, shapes, and diameter distributions; zinc oxide, aluminum oxide, aluminum hydroxide, iron red, yellow oxide, black iron oxide, cerium oxide, zirconium oxide, silica, mica, talc, sericite, boron nitride, barium sulfate, mica titanium having pearl-like gloss, and composites thereof; various pigments and colorants; water; and perfumes. The inorganic compounds such as titanium oxide and zinc oxide may be previously provided with a silicone process, a fluorine process, a metal soap process, or any other process before use.

Additionally or alternatively, the cosmetic product may contain resin particles of, for example, poly(methyl acrylate), nylon, silicone resin, silicone rubber, polyethylene, polyester, and polyurethane.

Further, the cosmetic product may contain, as active ingredients having whitening effects, for example, arbutin, kojic acid, vitamin C, sodium ascorbate, magnesium ascorbate phosphate, ascorbyl dipalmitate, glucoside ascorbate, other ascorbic acid derivatives, a placenta extract, sulfur, plant extracts such as an oil-soluble licorice extract and a mulberry extract, linoleic acid, linolenic acid, lactic acid, and tranexamic acid.

Furthermore, the cosmetic product may contain, as active ingredients effective in improving rough dry skin, for example: anti-aging active ingredients such as vitamin C, carotinoid, flavonoid, tannine, caffeic derivatives, lignan, saponin, retinoic acid and retinoic acid structural analogue, N-acetylglucosamine, and α-hydroxy acid; polyhydric alcohols such as glycerine, propylene glycol, 1,3-butylene glycol; saccharides such as mixed high-fructose, trehalose, and pullulan; biopolymers such as sodium hyaluronate, collagen, elastin, chitin, chitosan, and sodium chondroitin sulfate; amino acid, betaine, ceramide, sphingolipid, cholesterol, and derivatives thereof; ε-amino caproic acid, glycyrrhetinic acid, and various vitamins.

Moreover, it is also possible to use cosmetic ingredients described in, for example, Japanese Standard of Quasi-drug Ingredients 2006 (YAKUJI NIPPO LIMITED, Jun. 16, 2006) and in International Cosmetic Ingredient Dictionary and Handbook (The Cosmetic, Toiletry, and Fragrance Association, Eleventh Edition, 2006)

The cosmetic products as described above may be manufactured by generally known methods. The cosmetic products may be used in various forms such as a powder, a cake, a pencil, a stick, a cream, a gel, mousse, and a liquid. Specific examples of the cosmetic products include: cosmetic products for washing, such as soap, cleansing foam, make-up remover cream; skincare cosmetic products for moisturizing, dryness prevention, treating acne, treating cuticle, massaging, treating wrinkle and sag, treating dullness and dark rings under eyes, blocking UV ray, whitening, and antioxidation; base makeup cosmetic products such as a powder foundation, a liquid foundation, a cream foundation, a mousse foundation, a pressed powder, and a makeup base; colored cosmetics such as an eye shadow, an eyebrow powder/pencil, an eyeliner, mascara, and a lipstick; hair-care cosmetics for hair restoration, prevention of dandruff, prevention of itchiness, washing hair, conditioning/styling hair, perming or curling hair, and coloring and bleaching hair; body-care cosmetics for washing, sunscreen, preventing hands from becoming dry and rough, body slimming treatment, improving blood flow, alleviating itchiness, preventing body smell, antiperspirant, treating body hair, repellent, and a body powder; fragrance cosmetics such as a perfume, eau de parfum, eau de toilette, eau de cologne, shower cologne, solid perfume, body lotion, and bath oil; and oral health care products such as dentifrice and mouthwash.

EXAMPLES

The present invention will be described in detail below with reference to examples. Note that the present invention is not limited to the following examples.

Example 1

Using a rotary evaporator, 2 kg of a commercially available silica sol (SS-160, manufactured by JGC Catalysts and Chemicals Ltd.) having a mean particle diameter of 160 nm and a silica concentration of 20% by mass was concentrated to obtain 1 kg of a silica sol having a silica concentration of 40% by mass. A cation-exchange resin (SK-1B, manufactured by Mitsubishi Chemical; the same applies hereinafter) was added at once to the obtained silica sol to adjust the pH to 2.5. Thereafter, the cation-exchange resin was separated. As a result, a dealkalization treatment (e.g., removal of Na ions) was performed, thereby obtaining slurry a containing silica-based microparticles at a concentration of 39.3% by mass. A polymer dispersion liquid obtained by mixing 0.4 kg of cellulose-based particles (CEOLUS®RC-N30, manufactured by Asahi Kasei Corporation) and 1.3 kg of deionized water was added to the slurry a, thereby obtaining slurry b.

The obtained slurry b was used as a spray liquid. The spray liquid was sprayed and dried using a spray drier (NIRO-ATOMIZER, manufactured by NIRO). Specifically, the slurry was supplied at a flow rate of 2 L/hr. through one of two fluid nozzles and gas was supplied through the other nozzle at a pressure of 0.4 MPa into dry airflow with an inlet temperature set to 220° C. and an outlet temperature set to 50-55° C., and thus the slurry was sprayed and dried. The spray-dried slurry was passed through a 250-mesh sieve (a JIS standard test sieve). In this manner, organic-inorganic composite particles were obtained. Table 1 shows the preparation conditions for the organic-inorganic composite particles of Examples. The physical properties of powers of the organic-inorganic composite particles were measured by the following methods. Table 2 shows the measurement results.

(1) Method of Measuring Respective Mean Particle Diameters ($d_1$), ($d_2$), and ($d_4$) of the Organic-Inorganic Composite Particles, Silica-Based Particles, and Biodegradable Plastic Particles.

Particle size distributions of the respective particles were measured by the laser diffraction method. Based on the particle size distributions, the mean particle diameter ($d_1$) of the organic-inorganic composite particles, the mean particle diameter ($d_2$) of the silica-based particles, and the mean particle diameter ($d_4$) of the biodegradable plastic particles represented by the median diameter were determined. The measurement of the particle size distributions by the laser diffraction method was carried out using the laser diffraction/scattering particle size distribution analyzer LA-950v2 (manufactured by HORIBA, Ltd.).

(2) Mean Particle Diameter Ratio Depending on Ultrasonic Dispersion

When the mean particle diameter of the organic-inorganic composite particles was measured using the laser diffraction/scattering particle size distribution analyzer LA-950v2, the dispersion condition of the analyzer was set to "ultrasonic dispersion for 60 minutes". Following the ultrasonic dispersion, a particle size distribution was measured, and a mean particle diameter ($d_3$) represented by the median diameter was determined from the measured particle size distribution. The mean particle diameter ratio between the mean particle diameters ($d_3$) and ($d_1$) depending on ultrasound dispersion is written as ($d_3/d_1$).

(3) Method of Measuring a Particle Density of the Organic-Inorganic Composite Particles About 30 ml of the organic-inorganic composite particles were put in a porcelain crucible (type B-2) and dried at 105° C. for 2 hours. Thereafter, the organic-inorganic composite particles were cooled to room temperature in a desiccator. Next, 15 ml of the sample was taken and the absolute specific gravity thereof was measured using an automatic pycnometer (Ultrapyc1200e, manufactured by Quantachrome Instruments). The obtained measurement value was defined as the particle density.

(4) Method of Measuring a Coefficient of Variation of the Silica-Based Particles A photograph (SEM photograph) was taken with a magnification of 20,000 to 250,000 using the scanning electron microscope (JSM-7600F, manufactured by JEOL Ltd.). The mean particle diameter of 250 particles in this photograph was measured using an image analyzer (IP-1000, manufactured by Asahi Kasei Corporation). The coefficient of variation (CV value) in relation with the particle size distribution was calculated.

(5) Method of Measuring a Sphericity of the Silica-Based Particles

A photograph projection was obtained by photographing the silica-based particles with a magnification of 20,000 to 250,000 using a transmission electron microscope (H-8000, manufactured by Hitachi, Ltd.), and arbitrary 50 particles were selected from the photograph projection. For each of the selected particles, the maximum diameter (DL) and the short diameter (DS) orthogonal to the maximum diameter (DL) were measured, and the ratio (DS/DL) was obtained. The mean value of the ratios was determined as the sphericity.

(6) Method of Measuring a Specific Surface Area of the Organic-Inorganic Composite Particles About 30 ml of the organic-inorganic composite particle powder was put in a porcelain crucible (type B-2) and dried at 105° C. for two hours. Thereafter, the organic-inorganic composite particle powder was cooled to room temperature in a desiccator. Next, 1 g of the sample was taken and the specific surface area ($m^2/g$) thereof was measured by the BET method using a full-automatic surface area measuring device (Multisorb 12, manufactured by Yuasa Ionics Inc.). The measured specific surface area was converted with a specific gravity (e.g., 2.2 $g/cm^3$ if silica constitutes 100%, 1.5 $g/cm^3$ if cellulose constitutes 100%) which was converted with the composition ratio (mixing weight ratio) of the silica and the biodegradable plastic contained in the organic-inorganic composite particles. In this manner, the specific surface area per unit volume was obtained.

(7) Method of Measuring a Pore Volume and Pore Diameter of the Organic-Inorganic Composite Particles In a crucible, 10 g of the organic-inorganic composite particle powder was dried at 300° C. for one hour. The powder was then cooled to room temperature in a desiccator. The measurement was conducted by a mercury porosimetry method using an automatic porosimeter (PoreMasterPM33GT, manufactured by Quantachrome Instruments). Mercury was injected at a pressure from 1.5 kPa to 231 MPa. The pore size distribution was obtained from the relation between the pressure and the pore diameter. According to this method, mercury was injected into the pores from approximately 7 nm to approximately 1000 µm. Therefore, both the small-diameter pores existing in the porous silica-based particles and the large-diameter space (the measurement indicates that the space has a size of approximately ⅕ to ½ of the mean particle diameter of the porous silica-based particles) between the porous silica particles are measured. Based on the results of measurement of the small-diameter pores excluding the large-diameter space, the pore volume, the most frequent pore diameter (Dm), the minimum pore diameter (D0), and the maximum pore diameter (D100) were calculated. Here, the peak separation software (attached to the automatic porosimeter) was used as necessary.

(8) Method of Analyzing a Composition of the Organic-Inorganic Composite Particles On a platinum plate, 0.2 g of the organic-inorganic composite particle powder was precisely weighted. Then, 10 ml of sulfuric acid and 10 ml of hydrofluoric acid were added thereto and the mixture was heated on the sand bath until the white smoke of sulfuric acid came. After the mixture was cooled, about 50 ml of water was added and the mixture was dissolved by heat. After the mixture was cooled, the mixture was diluted into 200 ml of water, and the resulting mixture was treated as a test solution. With this test solution, the composition of the organic-inorganic composite particles was determined using an inductively coupled plasma emission spectrometer (ICPS-8100, Analysis software ICPS-8000, manufactured by SHIMADZU CORPORATION).

(9) Method of Measuring a Contact Angle

Following drying of 1 g of the organic-inorganic composite particles at 200° C., the particles were put into a cell having a diameter of 1 cm and a height of 5 cm, and then pressed with a load of 50 kgf, thereby obtaining a pressed mass of particles. A drop of water was put onto the pressed mass, and a contact angle with water was measured.

(10) Method of Measuring the Modulus of Elasticity

From the organic-inorganic composite particle powder, one particle which was within the range of ±0.5 µm with respect to the mean particle diameter was taken as a specimen. A modulus of elasticity in compression of the specimen was measured using a micro compression tester (MCTM-200, manufactured by SHIMADZU CORPORATION), while a load was applied to the specimen at a constant load rate. The same process was repeated four times to measure the moduli of elasticity in compression of five specimens in total. The average of the measured moduli was determined as the compression strength of the particles.

(11) Texture Characteristics of the Organic-Inorganic Composite Particles

Twenty specialized panelists conducted a sensory test on powders of the respective organic-inorganic composite particles, and the following seven items were evaluated by hearing from the twenty panelists: the smoothness, the moistness, the rolling effect, the uniform spreadability, the adhesiveness to skin, the duration of rolling effect, and the softness. The results were evaluated based on the following criteria (a). Moreover, the points given by the panelists were totaled and the texture of the organic-inorganic composite particles was evaluated based on the following evaluation criteria (b). Table 3 shows the results.

(12) How Users Feels when Using Powder Foundations

Powder foundations each including the powder of the organic-inorganic composite particles at the mixing rates (wt. %) shown in Table 4 were formed. Specifically, the powder (component (1)) according to Example 1 and components (2) to (9) were put into a mixer and agitated until they were mixed uniformly. Next, cosmetic ingredients (10) to (12) were added into this mixer and agitated and further mixed uniformly. Next, the resultant cake-like substance was pulverized and then about 12 g was extracted therefrom. The extracted pulverized substance was press-molded in a square metal plate of 46 mm×54 mm×4 mm; thus, the powder foundation was obtained. The twenty specialized panelists conducted a sensory test on the thus obtained powder foundations. The following six evaluation items were examined by hearing from the twenty panelists: (1) uniform spreadability, the moistness, and the smoothness during the application onto the skin; and (2) the uniformity, the moistness, and the softness of the cosmetic film after the application onto the skin. The results were evaluated based on the following criteria (a). Moreover, the points given by the panelists were totaled and how the panelists felt when using the foundations was evaluated based on the following evaluation criteria (b). Table 5 shows the results.

Evaluation Criteria (a)
5 points: Excellent
4 points: Good
3 points: Average
2 points: Poor
1 point: Very poor Evaluation Criteria (b)
Double circular mark: 80 or more points in total
Single circular mark: 60 or more and less than 80 points in total
White triangular mark: 40 or more and less than 60 points in total
Black triangular mark: 20 or more and less than 40 points in total
Cross mark: less than 20 points in total Example 2

Using a rotary evaporator, 50 g of a commercially available silica sol (SS-300, manufactured by JGC Catalysts and Chemicals Ltd.) having a mean particle diameter of 300 nm and a silica concentration of 20% by mass was concentrated to obtain 25 g of a silica sol having a silica concentration of 40% by mass. A cation-exchange resin (SK-1B, manufactured by Mitsubishi Chemical) was added at once to the silica sol to adjust the pH to 2.5. Thereafter, the cation-exchange resin was separated. As a result, a dealkalization treatment (e.g., removal of Na ions) was performed, thereby obtaining slurry a containing silica-based microparticles at a concentration of 39.3% by mass. A polymer dispersion liquid obtained by mixing 10 g of cellulose-based particles (CEOLUS®RC-N30, manufactured by Asahi Kasei Corporation) and 30 g of deionized water was added to the slurry a, thereby obtaining slurry b.

The obtained slurry b was mixed into a solution obtained by mixing 1300 g of heptane (manufactured by KANTO CHEMICAL CO., INC.) and 9.75 g of a surfactant (AO-10V, manufactured by Kao Corporation) together. The resultant mixture was emulsified at 10,000 rpm for 10 minutes, using an emulsifier/disperser (T.K. Robomix, manufactured by PRIMIX Corporation). The obtained emulsified liquid was heated at 60° C. for 16 hours, and then filtered using a Buchner funnel (3.2 L, manufactured by SEKIYARIKA CO., LTD.) and quantitative filter paper (No. 2, manufactured by Advantec Toyo Kaisha, Ltd.). The filtered substance was washed repeatedly with heptane to remove the surfactant, and a cake-like substance was obtained. The obtained cake-like substance was dried at 120° C. for 12 hours. This cake-like substance was pulverized in a juicer mixer (manufactured by Hitachi, Ltd.) for 10 seconds, and then passed through a 250-mesh sieve (a JIS standard test sieve), thereby obtaining organic-inorganic composite particles. The obtained particles were evaluated in the same manner as in Example 1.

Example 3

Organic-inorganic composite particles were prepared and measured in the same manner as in Example 1, except that a polymer dispersion liquid contained 0.17 kg of the cellulose-based particles (CEOLUS®RC-N30, manufactured by Asahi Kasei Corporation).

Example 4

Organic-inorganic composite particles were prepared in the same manner as in Example 1, except that a polymer dispersion liquid contained 0.93 kg of the cellulose-based particles (CEOLUS®RC-N30, manufactured by Asahi Kasei Corporation).

Example 5

Organic-inorganic composite particles were prepared in the same manner as in Example 3, except that 0.02 kg of a commercially available silica sol (SI-550, manufactured by JGC Catalysts and Chemicals Ltd.) having a mean particle diameter of 5 nm and a solid content concentration of 20% by mass was used as the silica sol and that no concentration using an evaporator was performed. The Organic-inorganic composite particles were measured in the same manner as in Example 1.

Example 6

Organic-inorganic composite particles were prepared and measured in the same manner as in Example 1, except that the two fluid nozzles supplied gas at a different pressure, i.e., 0.1 Mpa.

Comparative Example 1

Organic-inorganic composite particles were prepared and measured in the same manner as in Example 1, except that a polymer dispersion liquid contained 0.02 kg of the cellulose-based particles (CEOLUS®RC-N30, manufactured by Asahi Kasei Corporation).

Comparative Example 2

Organic-inorganic composite particles were obtained in the following manner: 0.01 kg of hexamethyldisilazane (SZ-31, manufactured by Shin-Etsu Chemical Co., Ltd.) having a molecular weight of 161.4 and 0.37 kg of methanol (a reagent chemical) were added to 0.1 kg of the organic-inorganic composite particles according to Example 1; The obtained liquid mixture was agitated at an output of 5 Hz for 10 minutes using a mixer (FM5C/I, manufactured by NIPPON COKE & ENGINEERING. CO., LTD.), and then, heated at 120° C. for 16 hours, thereby obtaining organic-inorganic composite particles. The obtained particles were measured in the same manner as in Example 1.

Comparative Example 3

Organic-inorganic composite particles were prepared in the same manner as in Example 3, except that a commercially available silica sol (SI-550, manufactured by JGC Catalysts and Chemicals Ltd.) having a mean particle diameter of 5 nm and a solid content concentration of 20% by mass was used as the silica sol, and that no concentration using an evaporator was performed. The particles were measured in the same manner as in Example 1.

TABLE 1

| | Slurry a Silica component (I) | | | | Polymer dispersion liquid | | Slurry b | Spray dry conditions | |
|---|---|---|---|---|---|---|---|---|---|
| | | Silica-based particles | | | Cellulose-based particles (II) | | Solid content | | |
| | | Mean | | | | Mean | | | |
| | | particle | Coefficient | | | particle | | | |
| | Type of silica component | diameter ($d_2$) (nm) | of variation (%) | Sphericity | Type of third component | diameter ($d_4$) (nm) | weight mixing ratio (I/II) | Spraying rate (liter/hour) | Spraying pressure (Mpa) |
| Example 1 | A | 160 | 9.0 | 0.89 | <1> | 300 | 50/50 | 1 | 0.4 |
| Example 2 | B | 300 | 8.0 | 0.93 | <1> | 300 | 50/50 | — | — |
| Example 3 | A | 160 | 9.0 | 0.89 | <1> | 300 | 70/30 | 1 | 0.4 |
| Example 4 | A | 160 | 9.0 | 0.89 | <1> | 300 | 30/70 | 1 | 0.4 |
| Example 5 | C | 5 | 9.0 | 0.94 | <1> | 300 | 1/99 | 1 | 0.4 |
| Example 6 | A | 160 | 9.0 | 0.89 | <1> | 300 | 50/50 | 1 | 0.1 |

TABLE 1-continued

| | Slurry a Silica component (I) | | | | Polymer dispersion liquid Cellulose-based particles (II) | | Slurry b Solid content | Spray dry conditions | |
|---|---|---|---|---|---|---|---|---|---|
| | | Silica-based particles | | | | | | | |
| | Type of silica component | Mean particle diameter ($d_2$) (nm) | Coefficient of variation (%) | Sphericity | Type of third component | Mean particle diameter ($d_4$) (nm) | weight mixing ratio (I/II) | Spraying rate (liter/hour) | Spraying pressure (Mpa) |
| Example 7 | D | — | — | — | <1> | 300 | 50/50 | 1 | 0.1 |
| Example 8 | A | 160 | 9.0 | 0.89 | <2> | 300 | 50/50 | 1 | 0.1 |
| Comparative Example 1 | A | 160 | 9.0 | 0.89 | <1> | 300 | 99.5/0.5 | 1 | 0.4 |
| Comparative Example 2 | A | 160 | 9.0 | 0.89 | <1> | 300 | 50/50 | 1 | 0.4 |
| Comparative Example 3 | C | 5 | 9.0 | 0.94 | <1> | 300 | 70/30 | 1 | 0.4 |

Silica Component A: SS-160 manufactured by JGC Catalysts and Chemicals Ltd. (Mean particle diameter of 160 nm)
Silica Component B: SS-300 manufactured by JGC Catalysts and Chemicals Ltd. (Mean particle diameter of 300 nm)
Silica Component C: Cataloid SI-550 manufactured by JGC Catalysts and Chemicals Ltd. (Mean particle diameter of 5 nm)
Silica Component D: Silicate solution (solid content concentration of 5%)
Cellulose-Based Particles <1>: CEOLUS ®RC-N30, manufactured by Asahi Kasei Corporation
Cellulose-Based Particles <2>: BiNFi-s WMa-10002 manufactured by SUGINO MACHINE LIMITED

TABLE 2

| | | | Example 1 | Example 2 | Example 3 | Example 4 | Example 5 | Example 6 | Example 7 | Example 8 | Comp. Example 1 | Comp. Example 2 | Comp. Example 3 |
|---|---|---|---|---|---|---|---|---|---|---|---|---|---|
| Composite Particles | Mean particle diameter ($d_1$) | μm | 4.9 | 4.8 | 5.0 | 4.9 | 5.0 | 17.0 | 4.9 | 4.9 | 4.2 | 5.5 | 3.0 |
| | Particle density | g/cm$^3$ | 1.8 | 1.8 | 1.9 | 1.7 | 1.5 | 1.8 | 1.8 | 1.8 | 2.2 | 1.8 | 1.9 |
| | Specific surface area | m$^2$/cm$^3$ | 30 | 21 | 35 | 27 | 34 | 30 | 15 | 30 | 40 | 30 | 850 |
| | Pore volume | ml/g | 0.25 | 0.29 | 0.28 | 0.24 | 0.21 | 0.25 | 0.14 | 0.32 | 0.36 | 0.35 | 0.18 |
| | Contact angle | ° | 48 | 47 | 40 | 60 | 65 | 48 | 48 | 48 | 45 | 100 | 45 |
| | $d_2/d_1$ | | — | 0.03 | 0.01 | 0.01 | 0.01 | 0.01 | 0.00 | 0.01 | 0.06 | 0.01 | 0.01 |
| | Modulus of elasticity in compression | GPa | 15 | 15 | 10 | 17 | 3 | 15 | 15 | 15 | 31 | 15 | 20 |
| | Silica | % | 50 | 50 | 70 | 30 | 1 | 50 | 50 | 50 | 99.5 | 50 | 70 |
| | Cellulose-based particles | % | 50 | 50 | 30 | 70 | 99 | 50 | 50 | 50 | 0.5 | 50 | 30 |

[Texture Characteristics of the Organic-Inorganic Composite Particles]

The texture characteristics of the powders obtained in Examples and Comparative Example were evaluated in the same manner as in Example 1. Table 3 shows the evaluation results. The results show that the powders of Examples are highly suitable as texture improvers for cosmetic products, whereas the powers of Comparative Examples are not suitable as a texture improver.

[Texture Characteristics of the Organic-Inorganic Composite Particles]

The texture characteristics of the powders obtained in Examples and Comparative Example were evaluated in the same manner as in Example 1. Table 3 shows the evaluation results. The results show that the powders of Examples are highly suitable as texture improvers for cosmetic products, whereas the powers of Comparative Examples are not suitable as a texture improver.

TABLE 3

| Evaluation Specimens | Smoothness | Moistness | Rolling Effect | Uniform Spreadability | Adhesiveness to Skin | Duration of Rolling Effect | Softness |
|---|---|---|---|---|---|---|---|
| Example 1 | ○ | ○ | ○ | ○ | ○ | ○ | ○ |
| Example 2 | ○ | ○ | ○ | ◎ | ○ | ○ | ○ |
| Example 3 | Δ | ◎ | ○ | Δ | ◎ | Δ | ◎ |
| Example 4 | ◎ | Δ | ○ | ○ | Δ | ○ | Δ |
| Example 5 | Δ | ◎ | ○ | ▲ | ◎ | ▲ | ◎ |
| Example 6 | ◎ | Δ | ◎ | Δ | ▲ | ◎ | ▲ |
| Example 7 | Δ | ◎ | Δ | ○ | ◎ | ○ | ◎ |
| Example 8 | ○ | ◎ | ○ | ◎ | ○ | Δ | ○ |
| Comparative Example 1 | ○ | X | ◎ | Δ | ▲ | ◎ | X |
| Comparative Example 2 | ○ | ○ | ○ | ◎ | Δ | X | X |
| Comparative Example 3 | ○ | Δ | ○ | ○ | ▲ | ○ | Δ |

[How Users Feel when Using the Powder Foundations]

Each of the powders of Examples and Comparative Examples (Component (1)) and the components (2) to (9) at the mixing rates (wt. %) shown Table 4 were put in a mixer and agitated, to be mixed uniformly. Next, cosmetic ingredients (10) to (12) were added to the mixer and agitated and mixed uniformly. Each of the resultant cake-like substances was processed in the same manner as in Example 1, to obtain a cosmetic product.

TABLE 4

| | Cosmetic Components and Ingredients Forming Powder Foundation | Mixing Amount (wt. %) |
|---|---|---|
| (1) | Each of Powders of Examples 1 to 3 and Comparative Examples 1 to 3 | 10.0 |
| (2) | Sericite (Silicone Processed) | 40.0 |
| (3) | Talc (Silicone Processed) | 29.0 |
| (4) | Mica (Silicone Processed) | 5.0 |
| (5) | Titanium Oxide (Silicone Processed) | 7.0 |
| (6) | Yellow Iron Oxide (Silicone Processed) | 1.2 |
| (7) | Iron Red (Silicone Processed) | 0.4 |
| (8) | Black Iron Oxide (Silicone Processed) | 0.2 |
| (9) | Methylparaben | 0.2 |
| (10) | Dimethicone | 4.0 |
| (11) | Liquid Paraffin | 2.0 |
| (12) | Tri 2-glyceryl ethylhexanoate | 1.0 |

Next, how the panelists felt using the thus obtained cosmetic products (when applying the cosmetic product and after the application) was evaluated in the same manner as in Example 1. Table 5 shows the results. The results show that the cosmetic products A to C according to Examples are excellent either during or after the application. On the other hand, the cosmetic products a to c according to Comparative Examples are not very good.

TABLE 5

| Evaluation Samples | During Application | | | After Application | | |
|---|---|---|---|---|---|---|
| | Uniform Spreadability | Moistness | Smoothness | Uniformity of Film | Moistness | Softness |
| EXAMPLE 1 (Cosmetic Product A) | ○ | Δ | ○ | ◎ | ○ | ○ |
| Example 2 (Cosmetic Product B) | ◎ | ○ | ◎ | ◎ | ○ | ○ |
| Example 3 (Cosmetic Product C) | ○ | ◎ | ○ | Δ | ◎ | ◎ |
| Comparative Example 1 (Cosmetic Product a) | ◎ | X | X | Δ | Δ | X |
| Comparative Example 2 (Cosmetic Product b) | ◎ | X | ▲ | ◎ | Δ | X |
| Comparative Example 3 (Cosmetic Product c) | ○ | X | Δ | ○ | ▲ | Δ |

The invention claimed is:

1. Organic-inorganic composite particles comprising a silica component and a biodegradable plastic, wherein
   the organic-inorganic composite particles have a mean particle diameter ($d_1$) ranging from 0.5 μm to 25 μm, an absolute specific gravity greater than 1.0 g/cm³ and equal to or smaller than 2.0 g/cm³, and a contact angle with water of 90° or less.

2. The organic-inorganic composite particles of claim 1, wherein
   the organic-inorganic composite particles have a specific surface area per unit volume, determined by a BET method, ranging from 5 m²/cm³ to 60 m²/cm³.

3. The organic-inorganic composite particles of claim 1, wherein
   the organic-inorganic composite particles have a modulus of elasticity ranging from 2 GPa to 30 GPa.

4. The organic-inorganic composite particles of claim 1, wherein
   the organic-inorganic composite particles have a mean particle diameter ($d_3$) after being subjected to ultrasonic dispersion in which a dispersion liquid of the organic-inorganic composite particles is ultrasonically dispersed for 60 minutes using an ultrasonic disperser, and
   a ratio ($d_3/d_1$) between the mean particle diameter ($d_3$) after the ultrasonic dispersion and the mean particle diameter ($d_1$) before the ultrasonic dispersion is within the range of ±0.05.

5. The organic-inorganic composite particles of claim 1, wherein
   the organic-inorganic composite particles include the silica component at a rate from 1 wt. % to 80 wt. %, and the biodegradable plastic at a rate from 20 wt. % to 99 wt. %.

6. The organic-inorganic composite particles of claim 1, wherein
   the silica component is configured as silica-based particles having a mean particle diameter ($d_2$) ranging from 5 nm to 1 μm.

7. The organic-inorganic composite particles of claim 1, wherein
   the biodegradable plastic is configured as biodegradable plastic particles having a mean particle diameter ($d_4$) ranging from 1 nm to 1 μm.

8. A cosmetic product comprising the organic-inorganic composite particles of claim 1.

* * * * *